(12) United States Patent
Marchand

(10) Patent No.: US 11,471,213 B2
(45) Date of Patent: Oct. 18, 2022

(54) MARCHAND ADVANCED SINGLE PORT HYSTERECTOMY—A LAPAROSCOPIC SURGICAL TECHNIQUE

(71) Applicant: Greg Marchand, Mesa, AZ (US)

(72) Inventor: Greg Marchand, Mesa, AZ (US)

(*) Notice: Subject to any disclaimer, the term of this patent is extended or adjusted under 35 U.S.C. 154(b) by 443 days.

(21) Appl. No.: 16/724,127

(22) Filed: Dec. 20, 2019

(65) Prior Publication Data

US 2021/0186598 A1    Jun. 24, 2021

(51) Int. Cl.
*A61B 18/14* (2006.01)
*A61B 1/313* (2006.01)
*A61B 1/04* (2006.01)
*A61B 18/12* (2006.01)
*A61B 18/00* (2006.01)
*A61B 17/42* (2006.01)
*A61B 17/34* (2006.01)

(52) U.S. Cl.
CPC ............ *A61B 18/1445* (2013.01); *A61B 1/04* (2013.01); *A61B 1/3132* (2013.01); *A61B 17/3423* (2013.01); *A61B 17/4241* (2013.01); *A61B 2018/00559* (2013.01); *A61B 2018/00595* (2013.01); *A61B 2018/00601* (2013.01); *A61B 2018/00982* (2013.01); *A61B 2018/126* (2013.01); *A61B 2018/1253* (2013.01); *A61B 2018/1422* (2013.01); *A61B 2018/1457* (2013.01)

(58) Field of Classification Search
CPC ..... A61B 18/1445; A61B 1/04; A61B 1/3132; A61B 17/3423; A61B 17/4241; A61B 2018/00559; A61B 2018/00595; A61B 2018/00601; A61B 2018/00982; A61B 2018/1253; A61B 2018/126; A61B 2018/1422; A61B 2018/1457
See application file for complete search history.

(56) References Cited

U.S. PATENT DOCUMENTS

| | | | | |
|---|---|---|---|---|
| 2012/0330324 | A1* | 12/2012 | Sauer | A61B 90/30 606/119 |
| 2014/0358158 | A1* | 12/2014 | Einarsson | A61B 17/42 606/119 |
| 2016/0135798 | A1* | 5/2016 | Macleod | A61B 17/00234 606/114 |
| 2018/0325552 | A1* | 11/2018 | Weihe | A61B 17/42 |

* cited by examiner

*Primary Examiner* — Michael F Peffley
*Assistant Examiner* — Bo Ouyang

(57) ABSTRACT

This disclosure is relative to the field of laparoscopic surgery and gynecologic surgery. Specifically disclosed is a surgical technique for laparoscopic hysterectomy and bilateral salpingectomy-oophorectomy which encompasses dissection and removal of the uterus, fallopian tubes, and ovaries. The technique utilizes a single-entry port located at the umbilicus in conjunction with access through the vaginal opening to access and manipulate the organs within the abdominal cavity.

1 Claim, 3 Drawing Sheets

MARCHAND ADVANCED SINGLE PORT HYSTERECTOMY—A LAPAROSCOPIC SURGICAL TECHNIQUE

CROSS-REFERENCE TO RELATED APPLICATION

Original Non-Provisional Application.

FIELD OF THE DISCLOSURE

This disclosure is relative to the field of laparoscopic surgery and gynecologic surgery. Specifically disclosed is a surgical technique for laparoscopic hysterectomy and bilateral salpingectomy-oophorectomy which encompasses dissection and removal of the uterus, fallopian tubes, and ovaries. The technique utilizes a single-entry port located at the umbilicus in conjunction with access through the vaginal opening to access and manipulate the organs within the abdominal cavity. Also disclosed are patient prep, post-procedure care, and inter-surgery examination of surrounding organs.

BACKGROUND OF THE DISCLOSURE

A hysterectomy is an operation to remove the uterus from a female patient. The necessity for this operation may include various issues such as abnormal bleeding, uterine cancer, adenomyosis, or uterine fibroids causing persistent abdominal pain. Historically, this operation has been considered major surgery, however, with the advancements in laparoscopic techniques the physical trauma and recovery time have both been greatly reduced. Following removal of the uterus, it may be advantageous for the patient to additionally remove the fallopian tubes, a procedure known as a salpingectomy, and remove the ovaries, a procedure known as an oophorectomy, within the scope of a single operation.

One method to carry out the procedure involves an open Pfannenstiel laparotomy surgery which entails creating a large incision traversing across the pubic area to provide access to the organs within the abdominal cavity. The Pfannenstiel procedure often requires significant healing time and causes unsightly scars. An alternative method utilizing laparoscopy involves multiple entry ports wherein the dissected organ may be removed through one of the entry ports. While this surgery has benefits over the open surgery, including lower blood loss, decreased pain, shorter hospital stays, and faster recover, the removal of a larger organ through a small port may create complication.

The preferred method, disclosed herein, will focus on a laparoscopic procedure utilizing a single port with removal of the uterus through the vagina.

When this procedure is used with a combination of spinal and general anesthesia, the result is an incredible, ultra-minimally invasive technique which removes a majority of postoperative pain and suffering from a major surgery that many women need.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure but are intended to be illustrative only.

DETAILED DESCRIPTION OF EMBODIMENTS

This disclosure outlines a technique for performing a laparoscopic hysterectomy and bilateral salpingectomy-oophorectomy utilizing a single-entry port located at the umbilicus in conjunction with access through the vaginal opening to access and manipulate the organs within the abdominal cavity. Also disclosed herein are patient prep, post-procedure care, and inter-surgery examination of surrounding organs. Before outlining the procedure, it is relevant to identify the instruments and their positive attributes which aid in the surgical procedure.

Figure 1:
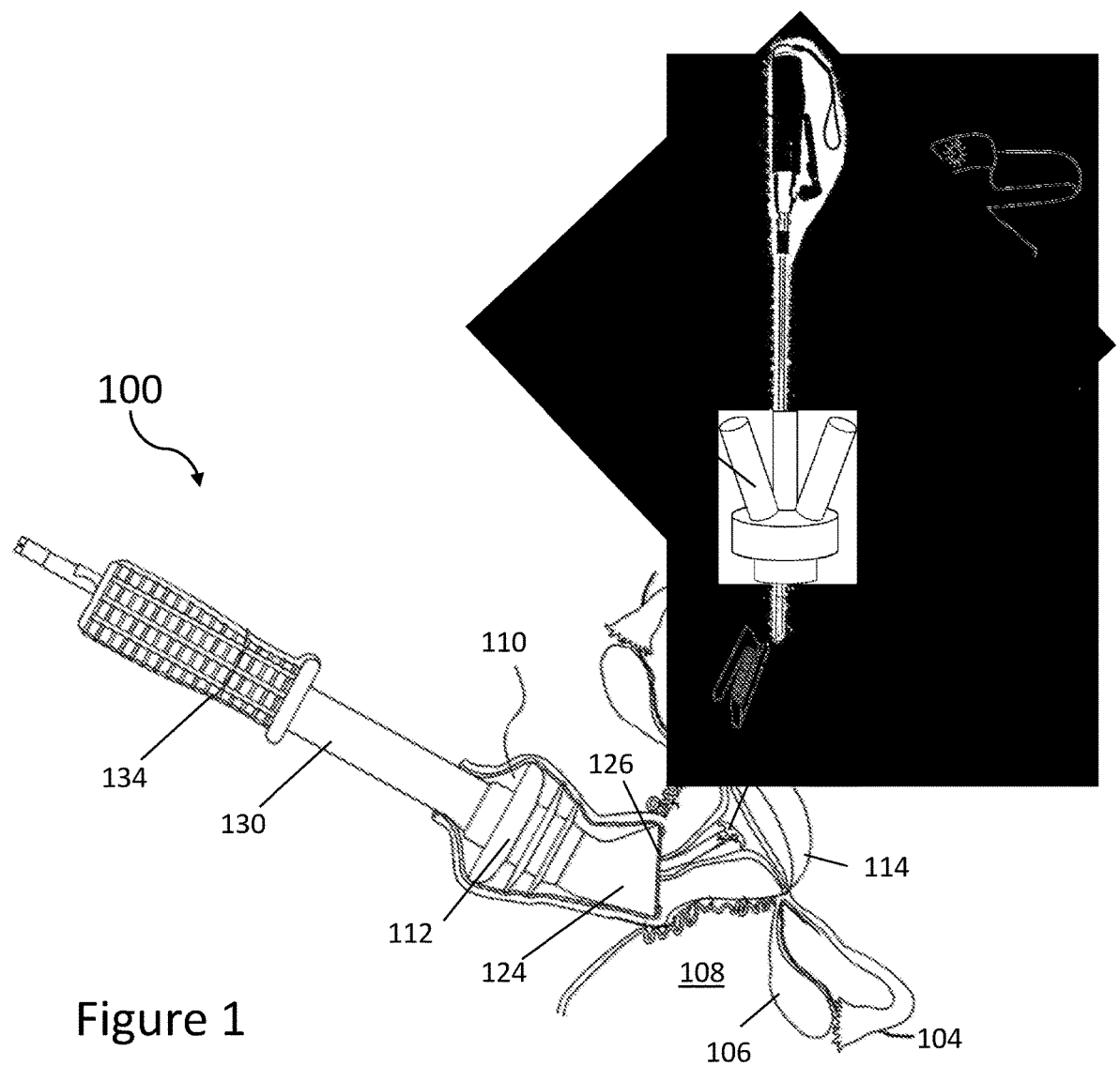
FIG. 1 shows the major surgical components in the abdominal cavity, in accordance with an embodiment of the present disclosure.
Figure 2:
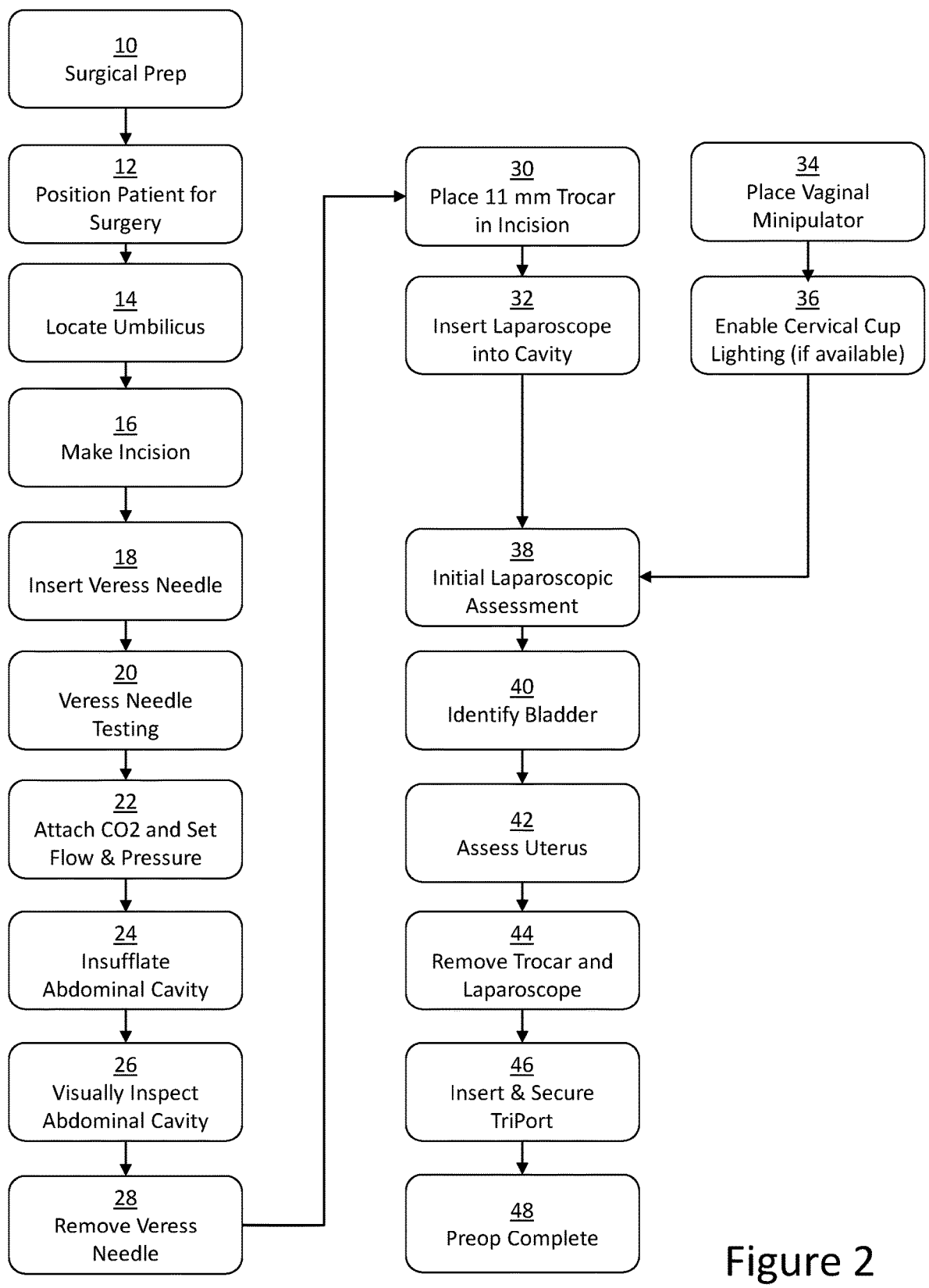
FIG. 2 shows a high-level workflow for the surgical procedure through surgical pre-op, in accordance with an embodiment of the present disclosure.
Figure 3:
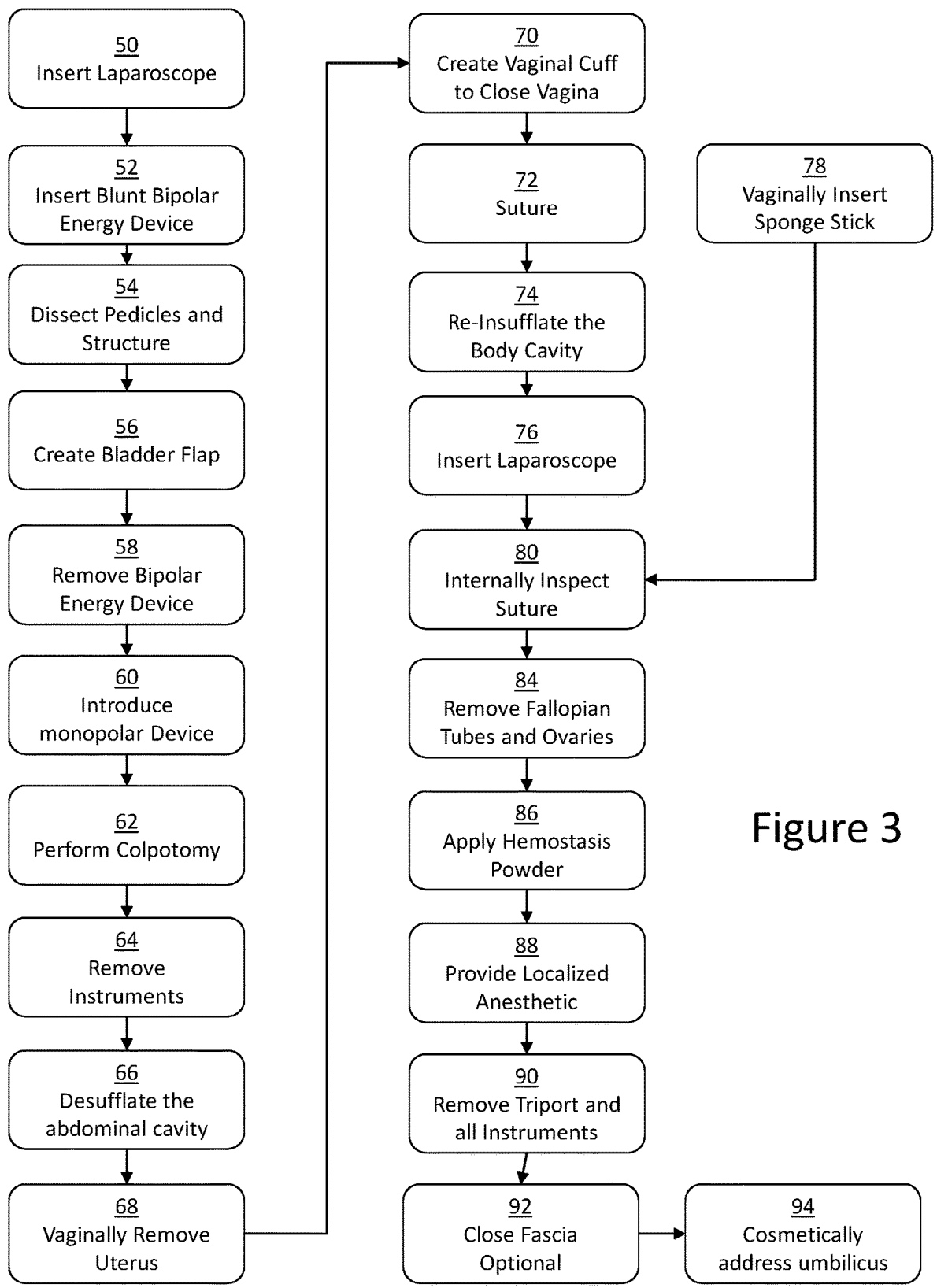
FIG. 3 shows a high-level workflow for the surgical procedure following surgical pre-op through completion, in accordance with an embodiment of the present disclosure.

In regard to the drawings and corresponding text, FIG. 1 identifies major surgical devices and anatomy with numbers 100+, while FIGS. 2 and 3 identify a step in the method are have numbers less than 100. Not all instruments are shown as they are generally known to the medical world and are prior art.

The following instruments are utilized in various embodiments of the disclosed method and may have non-generic preferential attributes which will be presented: bipolar electrical cautery device 116 or bipolar device, vaginal manipulator 130, trocars of various sizes, tri-port device 120, laparoscope 118, various graspers, a monopolar electrosurgery cauterizing device, a laparoscopic tenaculum, and an endoscopic kittner. In addition, some embodiments of the disclosed method may identify generic instruments common to surgery for use during the procedure including mechanical closure devices such as scalpel or mechanical cutting instrument, Veress needle and syringe, sutures or staples, surgical clips, sponge stick, catheter, towel clamps, and a suction irrigator. Devices to aid in positioning and prep of a patient for surgery may include lateral sleds and suspension apparatus for positioning the patient, and tape to secure body mass such that it does not interfere with the procedure.

The preferred bipolar electrical cautery device 116 utilized for the laparoscopic dissection currently available is the Ligasure manufactured by Covidien. This device, as shown in FIG. 1, comprises an opposing set of jaws 102 at the end of the shaft, wherein the jaws operate between and open and closed position and essentially bite into tissue. Electrical energy is applied to the tissue clamped within the jaws to both divide and simultaneously seal the blood vessels within the tissue by using the patient's collagen and elastin as a sealing agent. The jaws are in communication and controlled by a hand-held portion of the device located opposite the jaws. Within the Ligasure product line is the 5 mm blunt instrument, which for this procedure has advantages over other instruments with sharp points. Specifically, the other instruments having sharp plastic points often perform dissection into planes unintentionally and add complication to the procedure. Alternative acceptable devices include all devices that utilize bipolar energy, such as the brands Enseal, Thunderbeat, and the Tripolar devices.

The preferred choice of vaginal manipulator 130 is the Fornisee by McCarus-Volker. The Fornisee vaginal manipulator contains an adjustable uterine manipulator 122 comprising a rod of solid steel, thus allowing it to move any amount of tissue without bending. The rod is in communication with the handle 134 of the vaginal manipulator allowing rotation and manipulation of the rod. It also has a set of bellows 112 to lock into place in the uterus 110 and maintain pneumoperitoneum. The burning surface, which comprises a is a ridge along the lip of the cervical cup 124, is perfectly angled and is made of a hard, plastic-like substance that does not melt or change shape, even when burned directly with 50-watt coagulating monopolar current. In addition, the device provides an illuminated element light ring 126 at end of the cervical cup 124 next to the burning surface. This light ring provides the exact level of the colpotomy and is easily visible throughout the entire procedure. Alternatives for the vaginal manipulator include the Colpotomizer, Uterine ElevatOR PRO, V-Care, and the RUMI II (with the arch) and will be able to manipulate the uterus to expose every aspect.

Trocars for this procedure include any type of 11-millimeter blunt trocar, including reusable trocars, however, the preferred brand are the Ethicon trocar and the Covidien trocar. These types are desirable over alternatives as the product as the plastic point of the trocar include a type of plastic blade edge and are appropriate for abdominal placement.

The patient should be prepped in the dorsal lithotomy position and, if possible, the arms should be tucked 12. Individual consideration should be given for each obese patient. If a patient is so obese as to not allow the tucking of the arms at the side, then consideration should be given for lateral sleds, if possible, to aid in the appropriate placement of the patient. In all but the most obese patients, the arms should not be extended outward as this creates difficulty for the surgeon to access the appropriate anatomy. In the case where the patient is so obese that arms cannot be tucked or because of the unavailability of lateral arm sleds, extra-special precautions must be taken.

Laparoscopy usually does not require or amend itself to taping or manipulation of the pannus, but in the case where the patient is markedly obese, the surgeon will need to look at the operating field not only as an environment in which to perform the laparoscopic procedure, but also as a possible obstacle. Many of the taping and suspension devices utilized to perform laparoscopy can become time-consuming dangers when immediate laparotomy becomes necessary. With the understanding that every case must be customized based on the obesity of the patient as well as the equipment available in the particular operating room, every laparoscopy must be planned as if immediate conversion to laparotomy is imminent.

Following body positioning 12, anesthesia is provided to the patient prior to continuing the surgical operation.

In the preferred embodiment the best entry into the abdominal cavity is through the bottom of a natural umbilicus, herein simply umbilicus, in consideration of safety and approach. The term natural umbilicus is presented in opposition to an unnatural or neo-umbilicus which may be the result of plastic surgery on the abdomen. For patients with a neo-umbilicus, individual consideration must be given to the patient's surgical history as well as personal consideration of acceptable cosmesis.

Exploration of the umbilicus is initiated by apply pressure by the surgeon's finger at the bottom of the umbilicus of the anesthetized patient 14. In doing so, the surgeon is literally holding their finger directly against the patient's fascia 132. With the exception of the case where the surgeon cannot reach the bottom of the umbilicus, either because of scar tissue, no umbilicus exists, or the surgeon does not have a long enough finger, identification of this plane is standard approach in all obese patients.

The majority of obese patients have umbilici that can be manipulated manually to reveal the bottom. In the case of an extremely deep umbilicus, one approach is the use of a towel clamp which, because of its rounded head, will provide a view of the bottom of the umbilicus when plunged to the bottom of an obese patient's natural umbilicus. In this case, the towel clamp is inserted in the closed condition with a scalpel positioned in the closed jaws at the end of the clamp. Once positioned in the umbilicus, the clamp is opened and performs in a method similar to a 320-degree retractor for the walls of the patient's umbilicus.

Upon identifying the bottom of the umbilicus, an approximately one-centimeter incision should be made bottom of the umbilicus 16. In the preferred embodiment, this incision is made using a surgical scalpel with a number eleven blade. The number eleven blade is an elongated triangular blade sharpened along the hypotenuse edge with a strong pointed tip making it ideal for piercing to create a small incision. The blade is withdrawn after creating the incision.

After the incision is created, a Veress needle is introduced into the incision 18. Ideal entry into the abdominal cavity with the Veress needle includes tilting the Veress needle approximately 30 degrees toward the patient's feet and generally directly in the midline. In another embodiment, the Veress needle is inserted at a 45-degree angle at the umbilicus to avoid the bifurcation of the great vessels. In a patient with an elevated body mass index, a 75 to 90-degree angle is used since the umbilicus is caudal to the bifurcation. With a finger directly against the fascia, the surgeon inserts the pointed end of the needle until tactile feedback is identified by the surgeon as the needle punctures through the fascia.

In the field of laparoscopic surgery, alternative approaches such as an open or Hasson technique are commonly used when entering the central umbilical site. The Veress needle, however, has advantages over these alternative. Both entry techniques rely on a single, final step where one penetrates into the unknown layer. The difference with a Veress needle entry is that the Veress needle entry should enable the surgeon to know that he has penetrated somewhere he shouldn't have—as the return of feculent fluid or frank blood should clue the surgeon as to what error has occurred. When error occurs, such as the case of a bowel injury, a second attempt at laparoscopy can be made through a second site. In addition, the small, usually 9 gauge, Veress needle injury can be repaired without conversion to laparotomy. In the case of injury to major vasculature, a Veress needle's small caliber will prevent rapid blood loss, giving the surgeon time to convert the setting to a large laparotomy and mend the vessel. Conversely, an injury to a large vessel from a Hasson entry, will result in exsanguination in seconds, likely before any surgeon can achieve a laparotomy size-worthy for operative exploration.

To test the placement of the Veress needle, the surgeon continues with Veress needle testing 20. Veress needle testing includes attaching a syringe to the Veress needle which is then used, in no particular order, to inject saline, attempt to withdraw fluid from the abdominal cavity, and then demonstrate that fluid will fall through needle into the abdominal cavity when held plumb. If held perfectly plumb, when the lumen of the needle is filled with fluid the tendency of the fluid is to fall into the abdominal cavity, not to remain stagnant or to be pushed outward, secondary to the low pressure in the abdomen. If the Veress needle is embedded in solid tissue, such as the uterus, fluid cannot be injected.

Alternatively, in an inappropriate hollow location, such as the bowels, bladder or vasculature, feculent, bloody or urinous fluid may be drawn back. Lastly, the "drop" test of fluid falling in the abdominal cavity is to guard against a pre or post peritoneal entry and, conceivably in the hands of a diligent and experienced surgeon, guard against the unwanted insufflation of the preperitoneal or retroperitoneal spaces—as insufflation of either of these areas would confuse planes and make effective laparoscopy difficult or impossible.

Once the Veress needle is placed, a CO2 line is attached and the stopcock of the Veress needle is opened to insufflate 22 and 24. The surgeon then sets the rates of CO2 flow and maximum pressure, such as 15 mm to 20 mm Hg. He or she observes the intra-abdominal pressure and the total volume of CO2 infused as the abdomen enlarges and becomes tympanitic 26.

If placement of the Veress needle either does not pass Veress needle testing or the abdomen fails to enlarge, the surgeon may withdraw the needle at this point and attempt another Veress needle entry. This entry may be at an alternative angle, such as slanting the needle 30 degrees to the left or the right. In the case of an obese patient, the surgeon may change the angle for the second entry to be more toward the patient's feet, perhaps at an inflection of 15 degrees caudad. Following a second placement, the surgeon would again attempt to insufflate the abdominal cavity and, if unsuccessful a second time, switch to a direct entry method through the incision created in the umbilicus with a 5 mm blunt trocar.

Direct entry into the abdominal cavity with a blunt trocar is an excellent technique, however counter traction on the abdominal wall can be difficult to maintain, especially in patients with either too much or too little body fat. In this case, the surgeon may attempt to insufflate using the Veress needle from the left upper quadrant, which is common and presents a high success rate when umbilical entry fails.

Following insufflation with the Veress needle, the needle is withdrawn from the abdominal cavity 28, and, in the preferred embodiment, the surgeon will proceed to place an 11-millimeter blunt trocar through the incision in the umbilicus 30.

In the preferred embodiment, the surgeon then places a laparoscope through the trocar and into the abdominal cavity to perform an initial laparoscopic assessment 32 and 34. To gain insight, the 5 mm laparoscope may be placed a little deeper into the abdominal cavity to visualize the abdominal walls a centimeter or two away from the front scope. Next, do a 360-degree panoramic rotation around the abdomen and see what adhesions are still in place. The surgeon should avoid applying too much pressure on the laparoscope if adhesions trap the scope stuck in place.

As part of the inspection, the vaginal manipulator, which includes uterine manipulator, should be utilized to assess the qualities of the uterus 34. The device is inserted into the vaginal opening and should be positioned at any point prior to completing the initial laparoscopic assessment, which includes prior to making the first incision. As stated earlier, the preferred device will be the illuminated Fornisee device and lighting is enabled 36.

Continuing with the initial laparoscopic assessment 38 and with the manipulator 130 in place, the ring of the cervical cup 124 of the Fornisee should be illuminated to provide visibility of the cup edge 126. All other manipulators will require some wiggling at this point to enable the surgeon to visually identify the outline of the ring.

As part of the assessment, the surgeon must identify where the bladder stops 40. If the bladder is not completely visible, in one embodiment of the method, the surgeon may insert a Foley catheter directly into the bladder to engorge the bladder with a saline solution. Clear identification of the bladder prevents complications such as creating unnecessary bladder flaps or engaging it during the closing procedure.

In assessing the uterus 101 as part of the initial assessment, the surgeon should establish the size of the uterus and determine if it can be removed vaginally without morcellation 42. In addition, the surgeon must assess how pliable and soft is the uterus. This is accomplished by gently moving the uterus with the uterine manipulator to assess how much mobility the uterus has. In some cases, and for various reasons, the uterus may be non-pliable or geometrically challenging requiring either morcellation techniques to remove the uterus, or alternatively, the surgeon may determine the best course of action is to continue the hysterectomy laparotomy or utilize a multi-port laparoscopic technique.

As a final part of the initial laparoscopic assessment, in some embodiments the surgeon may gently challenge the anterior adhesions with the laparoscope, and possibly even separate small pedicles to assess assumptions.

In summary, the initial laparoscopic assessment 38 includes the following three steps. First, lighting the cervical cup of the vaginal manipulator and gently moving it to identify the incision ridge. Next, gently move the uterus with the uterine manipulator and assess how much mobility the uterus has. Lastly, gently challenge the anterior adhesions with the laparoscope.

Following the initial laparoscopic assessment, the next step is to remove the 11 mm blunt trocar in order to place a tri-port device 44 and 46. The preferred device for this procedure is the Tri-Port or Tri-Port+ 120 by Olympus. The Olympus TriPort+ is a minimally invasive, multi-instrument access device designed to facilitate laparo-endoscopic single site (LESS) surgery. The TriPort+ contains four instrument ports and two insufflation valves to support a range of four-instrument surgical procedures. The introducer ring, which aids in positioning the TriPort, is designed with a blunt tip allowing safe and easy introduction into the abdominal cavity by injecting the base ring through the single existing incision. Alternatively, the ring may be placed through the footprint of the 11 mm trocar port manually. The TriPort is self-adjusting to different incision lengths and accommodates abdominal wall thickness up to 10 cm.

When the 11 mm blunt trocar is removed, depending on the type of trocar utilized, the existing incision will either be almost exactly the same diameter as the introducer on the tripod, or slightly smaller. The surgeon simply matches up the introducer to the incision and inject the contents, which contain the plastic base ring and some of the plastic sheet of the Tri-Port 120 device, into the abdominal cavity. It is a rare complication for the ring to lodge between the peritoneum and the fascia, and if it does it is easy to withdraw the ring using the collapsible strap and then deploy the ring a second time.

With the ring in the abdominal cavity, the surgeon will firmly pull up on the sleeve, trim the sleeve, and install the TriPort device in the normal manner. The only exception, of course, is that the device is now installed through an 11-millimeter incision created by a blunt laparoscopic trocar, instead of the recommended size which ranges from 1.5 to 3 cm.

This concludes the preoperative setup for the Single Port Advanced Laparoscopic Hysterectomy 48.

The majority of the following procedure is completed through the TriPort 120 with the surgeon's dominant hand on the bipolar device 116 and the nondominant hand on the vaginal manipulator 130. Later in the surgery, this should then change, upon reaching the vaginal cuff, for a monopolar Bovie type device in the dominant hand. The third instrument that can be used either by the surgeon or by the assistant will vary according to the clinical scenario. Recommend devices include a 5 mm laparoscopic tenaculum (single tooth), a 5 mm endoscopic Kittner, and several different types of nontraumatic graspers available in case they are needed. In particular, is recommended that the surgeon has a 5 mm non-traumatic or wavy grasper available for any part of the procedure that requires it, as this instrument can be easily threaded between the two existing 5 mm instruments through the TriPort instrument ports for difficult portions of the procedure and removed for easier portions to reduce instrument interference. A suction irrigator should also be available, although my goal, and hopefully yours as well, will be to complete the procedure without enough blood loss to justify the use of the suction irrigator.

A common first step for laparoscopic surgery is to gain a field of vision into the abdominal cavity, and as such, a laparoscope 118 in inserted into one of the instrument ports of the TriPort device 50. In the preferred embodiment, an articulating scope is employed, however, the next recommended alternative would be a 5 mm, 30-degree laparoscope.

Next, a blunt bipolar electrical cautery device 116 such as the 5 mm blunt Ligasure device is inserted into one of the two remaining instrument ports of the TriPort Device 52.

As stated, the majority of the procedure should be performed with the main surgeon having one hand on the Ligasure™ and the other hand firmly on the uterine manipulator 130. The assistant will be used to expertly position the camera, especially in executing the advanced technique of positioning the camera in a more lateral than natural perspective in order to best use the 30-degree offset to best visualize the operating field. Care must be taken as to whether the camera is best positioned above or below the operating instrument based on the position of the uterus and the body habitus. If every movement of the operating instrument moves the camera as well, although this may be a necessary annoyance for difficult parts of the procedure, this is not the ideal circumstance for the entire procedure.

The disclosed procedure requires dissection of all the pedicles, from fallopian tubes 104 to the entrance of the vagina 110, with all-encompassing bites of bipolar energy 54. Each bite pulls together both leaves of the broad ligament 108, permanently sealing them together in perfect hemostasis, while pushing ever medial, leaving behind a sealed broad ligament, a removed uterus, and excellent hemostasis. Leaving the broad ligament unsealed invariably leads to bleeding, which leads to more lateral application of energy, and that leads to the necessity of cautery adjacent to the ureters. To prevent the last step of this cascade, we need to prevent the first. To do this, the surgeon needs a strong 5 mm bipolar device, and it needs to seal the leaves of the broad ligament as we progress through the procedure.

Dissection begins by cutting support structures from the anterior end of the uterus and progress by moving forward towards the posterior of the uterus, taking the major pedicles of the uterus, including the fallopian tubes, round ligament, both leaves of the broad ligament, the cardinal ligament and the uterine artery. The jaws of the Ligasure 102 should combine as many of these support structures in as few bites as possible, the bites through the ligaments should be taken as aggressively as possible, and with each bite the jaws should be snug against the uterus 101. Using the recommended bipolar device, the Ligasure, will result in the sealing of the anterior and posterior lips of the leaves of the broad ligament 108, which will result in excellent hemostasis. In the preferred embodiment, the surgeon should push cephalad with the vaginal manipulator, so that you are actually performing the circumferential colpotomy on the ring of the cervical cup of the vaginal manipulator cephalad to the utero-sacral ligaments. The surgeon should leave the utero-sacral ligaments intact and attached to the vagina as a critical step of this hysterectomy and may have serious implications for preventing prolapse of organs later in the patient's life.

In addition, it is not appropriate at this point in the procedure to simultaneously attempt removal of the Fallopian tubes at the time of initial hysterectomy. The Fallopian tubes 104 should be removed later, after the uterus has been removed vaginally and even possibly until after the vaginal cuff has been sewn. Doing so limits danger to the ureters and removes unnecessary interference in visualization.

A concept central to this entire hysterectomy is that these bites should be taken directly against the uterus—if not within the uterus itself. This technique involves an unabashed dissection directly into the uterus and for each bite with the bipolar electrical cautery device, such as the Ligasure, the surgeon must take in the initial pedicle dissection, he or she must grasp the broad ligament and all adjacent structures and push into the uterus before cutting and burning. Clearly this technique is not amenable to any type of cancer surgery where the intention is to remove surrounding tissues to prevent the spread of cancer.

Bites should be taken on each side of the uterus until all ligaments are ligated and divided to the level of the circumferential colpotomy. Multiple burning of individual pedicles may be necessary at times, and as long as the plane of dissection is kept snug against the uterus, no fear of lateral energy spreading is needed, regardless of device.

The next task that must be accomplished is the creation of a bladder flap and the movement of the bladder out of the operating field. Clearly, this task will be best accomplished with good visualization of the interface between the bladder and the uterus. In the preferred embodiment, the pedicles on each side of the uterus are removed before turning attention to the bladder flap. Actual creation of the bladder flap is best made using the bipolar energy device after the uterine manipulator is used to push the uterus as laterally as possible to the patient's right side 56. This usually involves shifting the power device slightly to the right to come across the top of the isthmic portion of the uterus in order to create a plane in the uterine serosa. Radical pressure to move the uterus laterally from the vaginal manipulator can usually produce close to a 90-degree angle for this dissection.

With the uterus free from broad ligament and surrounding support structures, the surgeon may advance to performing a circumferential colpotomy and the bipolar energy device is removed from the TriPort 58.

The techniques for performing circumferential colpotomy depend heavily on the ability to sustain a pneumoperitoneum at time of colpotomy as the incision into the uterine wall will create a vent for the $CO_2$ to escape through the vagina. Various methods exist for creating a robust seal in the vagina channel. A superior practice will be the use of pre-manufactured pneumo-occluder balloons. These balloons can be useful for maintaining pneumoperitoneum; however, it is strongly recommend filling those balloons with saline instead of air and understanding ahead of time exactly how far you can get away with insufflating them without the balloon bursting. The preferred embodiment, once again, relies on the previously described Fornisee which has a rubber pneumo-occlusion ring that, once placed in the vagina, essentially never fails, regardless of the amount of manipulation.

You should begin the colpotomy after all pedicles have been dissected and the bladder has been pushed well out of the operating field 62. The recommended tool for performing the circumferential colpotomy will be the laparoscopic extended hook cautery attached to a hand-held monopolar Bovie device. The laparoscopic extended hook cautery enters through the TriPort+ device. The cautery should use coagulating current as there is no danger of stripping this area of the anatomy of its robust blood supply, and in a preferred embodiment, a setting of 35 watts of coagulating current is appropriate.

The colpotomy is performed by outlining around the edge of the cervical cup and along the burning surface with the coagulating hook, such as to dissect and cauterize the uterine wall by way of monopolar electrical energy. The surgeon completes the first half, (or 55-65%) of the colpotomy and then switch to the opposite side, ending at approximately the absolute top of the cervical cup 124. If the tissue has been properly denuded and all vessels ligated prior to the colpotomy, no further dissection is necessary, and that the surgeon can cleanly make the colpotomy in one pass. Although the ring formed by the cervical cup 124, even when coupled with a rod-like uterine manipulator 122, does not have the ability to swivel the vagina very much against the ring, the small amount of movement that can be performed can be extremely useful and, in difficult cases, allow the surgeon to visualize the start of the contralateral colpotomy allowing the incision to be completed in one motion.

The procedure has now completed the abdominal portion of the hysterectomy. With the instruments removed, the multiport device is left in the incision of the umbilicus and the abdomen may be desufflated 64 and 66. The remainder of the hysterectomy is performed through the vagina.

Vaginal removal of the uterus, regardless of its size, will be the preferred modality for completing this laparoscopic technique 68. Although most uteri will be able to be removed without "bivalving" (vaginal morcellation), the technique is a critical component of this surgery. In most cases, the uterus is free to passed through the vaginal channel to outside of the body. As the uterus typically has an elastic property, in many cases the uterus will remain attached to the vaginal manipulator and both are withdrawn together. If the uterus remain internal after the vaginal manipulator is removed, it may be withdrawn manually using forceps, grabbers, or digitally.

Following the removal, the next course of action is to close the vagina from the vaginal perspective. The vaginal cuff, located where the vagina that opens up into the peritoneum, is created by the surgeon suturing together the edges of the surgical site where the cervix was attached to the vagina 70. For the majority of women who had a vaginal delivery, closing the vagina from the vaginal approach is very fast and easy. One simply needs to grasp any aspect of the vaginal cuff that can easily be palpated in a Kocher clamp and perform a quick running locked suture, preferably with 0 vicryl or larger on a CT needle 72. This suture can easily be performed through a speculum and in rare cases and more difficult circumstances, assistance with vaginal retractors can be helpful.

Following completion of the vaginal suturing, the surgeon should immediately test the suture by gently pushing up either with their fingers or a vaginal sponge stick. A successful vaginal closure need not be airtight, but it should be successful to the point where a sponge stick when inserted in the vaginal approach cannot be visualized in the abdominal cavity at time of returning to laparoscopy. No part of the white sponge should be seen from the abdominal approach. In the preferred embodiment, closing the peritoneum abdominally and putting in some sutures vaginally is recommended.

At this point the surgeon should resume the abdominal aspect of the procedure and turn the insufflation back on 74. The abdominal cavity should again be visualized by introducing the laparoscope back into the abdominal cavity 76. The vaginal cuff should be visualized by gently pushing a sponge stick in the vagina under direct laparoscopic visualization. This check has two purposes. First, the surgeon must be sure that no part of the sponge on the sponge stick in the vagina is visual in the abdominal cavity and, if it is seen, consideration should be given for placing additional stitches from the vaginal perspective 80. Alternatively, one could place additional sutures from the abdominal perspective. As previously stated above, it is not necessary for the vaginal closure to be airtight, but it is critical that none of the sponge be visualized from the abdominal cavity. A second reason for testing the vaginal vault with the sponge stick, while visualizing laparoscopically, is to be sure that none of the bowels are attached to the suture line.

Once the uterus has been removed, the medial aspect of the Fallopian tubes should be easy to identify, in most cases, because of the burns. Removal of the Fallopian tubes on each side should be undertaken separately from removal of the ovaries, in order to minimize the amount of retroperitoneal tissue taken in each bite. A secondary grasper is generally not necessary, as this technique recommends placing only the bipolar energy device behind the Fallopian tube, and the Fallopian tube should be gently pulled medially in the abdominal cavity 84. The surgeon should have the jaws of the bipolar device snug against the Fallopian tube without any unnecessary tissue. In most cases, the Fallopian tubes may be removed laparoscopically through the TriPort. In an alternative embodiment, the Fallopian tubes may be removed either by passing them through the vaginal cavity prior to closing the vaginal cuff. In yet another embodiment, the Fallopian tubes may be removed through a trocar reinserted into the incision.

Following removal of the Fallopian tubes, removal of any ovaries that the patient wants removed should occur. The bipolar energy device should be placed behind the ovary and the ovary should be held as medial as possible, prior to activating the Ligasure device and cutting the ovarian ligaments. Pressure should be held medially with special care not to tear the ligaments. Pressure should be essentially as much as can be reasonably applied without fear of ripping the infundibular pelvic ligament. In most cases, the ovaries may be removed laparoscopically through the TriPort. In an alternative embodiment, the ovaries may be removed either by passing them through the vaginal cavity prior to closing the vaginal cuff. In yet another embodiment, the ovaries may be removed through a trocar reinserted into the incision.

This technique of keeping snug against the ovaries 106 has been criticized by several authors because of its risk of ovarian remnant syndrome. While this risk does exist, the risk of ovarian remnant syndrome and subsequent morbidity is quite small compared to the risk of ureteral injury, which is a devastating complication of hysterectomy. Therefore, it is recommended that only in select cases should surgeons abandon the technique of "snug" removal of the ovaries, perhaps in some chronic pain patients. The rationale is that, while dissection with the bipolar "snug" against the ovary does have the potential of leaving microscopic amounts of ovarian tissue, it is extremely valuable in avoiding injury in the adnexa.

Following the removal of the adnexa of the uterus, the abdomen and pelvis should again be surveyed, and special attention should be paid to the vaginal cuff. This includes placing one unit of powdered coagulant on the vaginal cuff to aid with hemostasis such as Arista or Surgicel Powder 86. The technique of placing a powered coagulant hemostatic agent is generally successful in stopping small areas of bleeding of the vaginal cuff, which will prevent hematoma and subsequent abscesses.

Anesthetic efforts including the injecting of 20 cc's of one-half percent Marcaine directly into the abdominal cavity, in all patients except those with extremely small body mass index, is appropriate 88. This injection can be easily soaked in by all pedicles and will help with the post-operative pain.

Finally, the TriPort 120 is removed from the incision 90. A laparoscopic closure system may be employed for a true closure of the fascia 132. One recommended example of the closure system is the Carter-Thomason system. Alternatively, when using only a single port, a fascial closure technique using S retractors or Army/Navy retractors will be acceptable.

For the majority of cases performed with this technique, however, there is likely no reason the fascia needs to be closed 92. The surgeon may inspect the umbilicus and the subcutaneous tissue and assess if the fascia is easily noticeable from gentle inspection using only pickups or Addison forceps. When the surgeon is able to visualize both sides of the fascia, the tissue planes should be closed using a 0 Vicryl on an UR 6 needle.

The closure of the subcutaneous tissue will enable the use of Dermabond glue onto the skin incision without the fear that this glue is going to enter the abdominal cavity—where it could be considered quite caustic.

It is also recommended that, in order to achieve the best results after placing the subcutaneous suture or fascial suture at the bottom of the umbilicus, gently push the umbilicus into the abdomen prior to putting the glue inside of it. This will return the umbilicus to a nice concave shape that, almost invariably, it will heal into permanently. This is both cosmetically pleasing to the patient and provides an excellent "tiny bowl" to pour the Dermabond™ glue into. Following the surgery, most patients find they have a smaller, more concave umbilicus than they previously had 94.

What is claimed is:

1. A surgical method performed by a surgeon for laparoscopically dissecting a uterus through a single-entry port located at a base of a patient's umbilicus and removing said uterus through a vaginal opening of the patient comprising the steps of:

utilizing a scalpel to create an incision through the at the base of the umbilicus;

introducing a trocar into the abdominal cavity of a patient through the incision;

inserting a distal end of a vaginal manipulator into the vaginal opening,
   wherein the vaginal manipulator comprises a handle at a proximal end of a shaft, a series of bellows are positioned along the shaft, a cervical cup, having a base axially positioned at the distal end of the shaft and an opening with a lip opposite the handle, and an uterine manipulator extending from the base of the cup and in communication with said handle and;
   wherein the opening of the cervical cup comprises a burning surface positioned along the lip of the cervical cup and which is illuminated by a light ring;

inserting a camera of a laparoscope through the trocar such that an internal view of the abdominal cavity can be visualized, and performing an initial laparoscopic assessment;

withdrawing first the laparoscope from the patient and then removing the trocar from the incision of the patient;

placing a multi-entry port device into the incision,
   wherein the multi-entry port device comprises a distal end configured to pass through the incision, and an proximal end configured to reside external to the patient; and
   wherein the multi-entry port device provides passage for a plurality of instruments from a point external to the patient and into the abdominal cavity;
   inserting the camera of the laparoscope and inserting a cutting end of a bipolar electrical cautery device through the multi-entry port device into the abdominal cavity,
   wherein the cutting end of bipolar electrical cautery device has a pair of opposing jaws configured to cauterize and dissect tissue;

dissecting the uterus from a series of support structures surrounding the uterus,
   while grasping a hand-held control of the bipolar electrical cautery device in the surgeon's dominant hand and the handle of the vaginal manipulator in the surgeon's non-dominant hand;

inserting a cutting end of a monopolar device through the multi-entry port device and into the abdominal cavity,
   wherein the cutting end of the monopolar device comprises a laparoscopic extended hook cautery attached to a hand-held monopolar device;

performing a colpotomy to detach the uterus,
   wherein the colpotomy comprises dissecting and cauterizing the uterine wall by outlining the cervical cup of the vaginal manipulator with the cutting end of the monopolar device;

vaginally withdrawing the vaginal manipulator and the detached uterus;

creating a vaginal cuff;

suturing along the vaginal cuff as to close the vagina; and applying a powdered coagulant along the vaginal cuff.

\* \* \* \* \*